United States Patent
Walker et al.

(10) Patent No.: US 6,245,056 B1
(45) Date of Patent: Jun. 12, 2001

(54) SAFE INTRAVENOUS INFUSION PORT INJECTORS

(76) Inventors: Jack M. Walker, 247 Echo La., Portola Valley, CA (US) 84028; Jack W. Shields, 1950 Las Tunas Rd., Santa Barbara, CA (US) 93103

( * ) Notice: Subject to any disclaimer, the term of this patent is extended or adjusted under 35 U.S.C. 154(b) by 0 days.

(21) Appl. No.: 09/249,712

(22) Filed: Feb. 12, 1999

(51) Int. Cl.$^7$ .................. A61M 25/16; A61M 25/18; A61M 39/02

(52) U.S. Cl. .................. 604/539; 604/533; 604/181; 604/183

(58) Field of Search .................. 604/181, 244, 604/264, 272, 403, 412–415, 905, 202, 200, 201, 239, 240, 243, 539, 183, 533, 523

(56) References Cited

U.S. PATENT DOCUMENTS

| | | | |
|---|---|---|---|
| 4,759,756 | * | 7/1988 | Forman et al. .................. 604/413 |
| 5,049,129 | * | 9/1991 | Zdeb et al. .................. 604/85 |
| 5,137,524 | * | 8/1992 | Lynn et al. .................. 604/283 |
| 5,221,272 | * | 6/1993 | Proni .................. 604/283 |
| 5,356,380 | * | 10/1994 | Hoekwater et al. .................. 604/85 |
| 5,620,008 | * | 4/1997 | Shinar et al. .................. 128/764 |
| 5,827,262 | * | 10/1998 | Neftel et al. .................. 604/414 |

* cited by examiner

*Primary Examiner*—Glenn K. Dawson
*Assistant Examiner*—Jennifer Maynard

(57) ABSTRACT

We describe connectors for safely and conveniently injecting measured doses of sterile liquid medications into a patient via one or more infusion ports in intravenous access assemblies. Each connector comprises a tubular injector divided by a rigid septum which holds a hollow needle sharp on each end safely recessed in a leading and in a trailing chamber. The leading chamber snugly holds the trailing limb and penetrable cap of an inserted standard infusion port. The trailing recess snugly holds the leading end of a cartridge with a leading penetrable diaphragm, a bore containing liquid medication, a cartridge piston and trailing bore suitable for insertion of a separate cartridge plunger having markers for measuring doses delivered; or, alternatively, the pentrable cap and trailing limb of second similar infusion port attached by trailing tubing to a large measured volume infusion source. When assembled such that the trailing cap of infusion port is penetrated by the needle in the leading chamber and the leading diaphragm of the cartridge or, alternatively, the leading penetrable cap on a second infusion port is penetrated by the needle in the trailing chamber, such that flow can proceed through the needle, precisely measured doses of sterile liquid medication can be injected into the venous access assembly without possibilities for the user to touch, get stuck or finger-contaminate the needle or its contents. Unique features added to increase the efficiency of the system are a biased leading end on the tubular injector to conveniently and securely accommodate a Y-infusion port; an eccentric needle in the connector, such that rotation prevents the leading sharp end of the needle from passing through the infusion port cap via the same track; and an easily removed biased cap for keeping the cartridge diaphragm sterile.

1 Claim, 3 Drawing Sheets

SAFE INTRAVENOUS INFUSION PORT INJECTORS

BACKGROUND OF THE INVENTION

1. Field of the Invention

Systems used currently to inject sterile fluid medications into patients via the ports of intravenous (IV) access assemblies pose hazards to patients and to health care workers. For patients, the principal hazard is blood stream infections with skin- or glove-borne microorganisms caused by contamination of exposed needles, syringes, multiple dose vial caps or recesses in infusion ports suitable for bacterial colonization. For healthcare workers, the principal hazards are accidental needlesticks from exposed sharp hollow-bore steel needles while handling the equipment essential to the IV injection of sterile fluid medications into patients. By eliminating multiple dose vials, syringes, exposed needles, needleless systems and minimizing chances for contamination of caps through which sterile fluid medications are injected, the connectors are designed to reduce these mutual hazards.

2. Description of the Prior Art

For forty years medication filled cartridges, called carpules, with leading diaphragms and trailing pistons insertable into stainless steel aspirating syringes have been used by dentists for injecting anesthetics prior to performing painful procedures. The needles used are sharp on each end and housed in an externally threaded hub. The leading end of the needle is exposed for giving the injection. The trailing end of the needle which penetrates the diaphragm in the leading end of the carpule is stabilized by the threaded hub which is affixable to the leading end of a carpule aspirating syringe. The carpule piston is activated by a finger activated plunger permanently affixed inside the trailing end of the carpule aspirating syringe having trailing external flanges for finger placement and breech- or side-loading means for insertion of the carpule. The leading end of the plunger is supplied with a harpoon which temporarily engages the carpule piston such that the user can aspirate fluid from a patient into the carpule, as well as discharge the fluid contents of the carpule into a patient via the exposed leading end of the needle. Such carpules are traditionally made of glass for containing sterile liquid contents. However, they are not supplied with caps to keep the leading diaphragms sterile, or supplied individually in sterile packages which keep the entire external surfaces sterile. Formerly, dentists were advised to sterilize the external surfaces of the diaphragms on the leading ends of carpules with local antiseptics before insertion into carpule aspirating syringes, but now such antisepsis is seldom practiced.

Eliminating use of stainless steel carpule aspirating syringes, some dentists use disposable injectors, such as the Monoject® 418 disposable carpule aspirating injector. These consist of a plastic tube with a needle sharp on each end molded into the leading end of the injector, a bore for insertion of the carpule, and a trailing reusable plunger housed in a snap-on assembly with a permanently contained plunger having a harpoon on the leading end, a body through which the plunger slides with thumb ring activation and external flanges for finger placement. The trailing end of the sharp needle is safely recessed in the injector for penetrating the diaphragm on the leading end of the carpule. The exposed leading end of the sharp needle is supplied with a slip-on scabbard which is removed and not replaced after the carpule is inserted and the snap-on assembly is attached. After use, the assembly which snaps onto flanges on the trailing end of the injector is removed for reuse, and the injector containing the carpule is disposed as a unit with the leading end of the sharp needle exposed.

Some dentists use a modification of the Monoject® 418 system exemplified in the Ultrasafe™ Aspirating Syringe. This system differs in that the disposable carpule injector is supplied with a permanently attached outer sleeve which slides over a tubular plastic carpule holder and locks to cover the exposed leading end of the sharp needle after use in a patient; and in that the plunger assembly is not detached from the injector after use.

In medical practice, cartridges with initially scabbard-protected leading permanently attached sharp needles, bores filled with sterile liquid medications and trailing pistons releasably attachable to inserted plungers have been used for more than fifty years. The Wyeth Tubex® is an example. These generally employ a threaded bolt embodied in the trailing end of the cartridge piston which mates with a threaded receptacle in the leading end of a plunger and finger holding assembly, sometimes called a syrette. The leading needle is embodied in the cartridge, instead of attached to or attachable to a syringe assembly into which the cartridge is inserted via a hinging breech which locks shut in the long axis of the injecting holder/cartridge assembly, and opens to eject the spent cartridge/needle after use in a patient.

For user safety, the Tubex® systems have been modified recently by using a blunt cannula instead of a sharp needle on the leading end of the cartridge, as in some systems sold by Wyeth for accessing slit caps on intravenous access ports; or by using a clamp-on reusable plunger and finger holding assembly which releasably attaches to the trailing end of the cartridge with a sharp needle or a blunt cannula on the leading end.

A computer search for an injector or connector containing a recessed needle sharp on each end for discharging the sterile medicinal contents of a cartridge or a carpule into an intravenous infusion port found none. In U.S. Pat. No. 5,120,324 (Jun. 9, 1992), Sancoff disclosed a protected IV injection site coupling having a trailing means for connection to IV tubing and a leading housing containing a recessed needle for accessing an IV infusion port having a penetrable elastomeric cap. The leading end of the needle housing was slit and supplied with internal flanges for grasping the trailing end of the elastomeric cap. In U.S. Pat. No. 5,281,206 (Jan. 25, 1994), Lopez described a connector with a recessed needle with a rotatable collar for locking attachment of an attachable filled syringe to a branch port of an intravenous fluid flow line, such that the leading end of the injector can be stabilized over the injection port. In U.S. Pat. No. 5,735,823 (Apr. 7, 1998), Berger described a safety syringe having a sliding sleeve which allows filling of a syringe from a vial and then, with forward displacement of the sleeve over the syringe, allows locking of the syringe to an intravenous access system by a receptacle in leading end of the sliding sleeve to the main stream carrying limb of a Y-port, such that the leading bevel and shank of the syringe attached needle are not exposed during or after injection of the syringe contents. Search for a bias on the leading end of the injector for cradling the elastomeric cap on a standard Y-port on an IV infusion assembly, along with a needle sharp on each end found none.

Needles sharp on each end are commonly used in Vacutainer™ systems wherein the trailing end of the needle is temporarily or permanently recessed in a Vacutainer tube holder. However, the leading end of the needle, even though initially covered with a disposable scabbard, must be exposed to access the vein of a patient.

The instant patent application differs primarily from patents for medical cartridges and dental carpules in common use in that the recessed injector needle sharp on each end does not entail the use of a standard syringe or other means for reversibly attaching a syringe plunger to a piston for aspirating fluid, as well as for injecting fluid medication into a patient. Because the system disclosed herein injects into an infusion port of an established IV access system, instead of directly into a patient, there is no need to aspirate lymph or blood-tinged fluid from the patient to be sure of accurate placement of the needle. If the system were designed to aspirate fluid from the main stream in an IV access system, aspiration might dilute the fluid in the cartridge and, thus, potentially interfere with accurate volumetric measurement of fluid medication actually injected.

Traditionally, the Y-ports and simple ports on IV infusion assemblies have been serviced by using a sharp hollow needle to fill an attached syringe from a single or multiple dose vial and, then, using the same needle-attached syringe to penetrate and inject sterile liquid medication through the penetrable cap on the infusion port into the stream line of the IV access assembly. However since 1992, fear of accidental needlesticks with sharp needles whose bores potentially contain human immunodeficiency virus (HIV), hepatitis B virus (HBV) or hepatitis B virus (HBV) spurred the development and use of needleless systems wherein blunt cannulae or syringe nozzles are used, instead of needles, to access modified infusion ports in IV infusion assemblies. A result has been a three to ten-fold increase in nosocomial blood stream infections in patients with skin- or glove-borne borne bacteria, when compared with the systems used traditionally. This increase appears partly owing to insufficient handwashing and use of unsterile gloves when handling the paraphernalia involved; and partly owing to recesses in the modified ports conducive to bacterial colonization with repeated use of blunt instruments passing through the same path of entry into the stream line.

The use of a shielded injector with or without a leading bias for cradling the elastomeric cap of a standard Y-infusion port was claimed in a patent, "Automatic Needle Shields for Safer Injections", currently pending for an elastomeric needle shielding system wherein the thrust of the needle beyond the leading end of the shield permits filling of a needle-attached syringe from a vial before injection into an IV access port. The instant disclosure differs in that a needle sharp on each end is permanently housed in a tubular injector, such that neither end of the needle is ever exposed to finger-touching during filling or use in a patient.

Fundamentally, the instant disclosure differs from the prior art in the following additional aspects:
1. The hollow bore needle sharp on each end is recessed such that neither end can be touched by a naked or a gloved finger.
2. The cartridge or carpule can be supplied only partially filled, such that the trailing bore of the cartridge behind the piston supplies space for snug and stable insertion of a separate simple plunger which not only activates the cartridge piston in a leading direction, but also can be used to measure dosage injected.
3. The leading end of the connector can be cut on a bias, such that leading end of the injector will not only cradle the elastomeric cap on a standard infusion port, but also gain stability by partly encircling the main stream limb of a Y-infusion port.
4. The hollow needle in the injector can be eccentric, instead of concentric, in the long axis of the injector/cartridge assembly such that, by planned rotation of the injector in the long axis, passage of the needle through the same track in the elastomeric cap of an IV access cap can be avoided.
5. The diaphragm on the leading end of the partly filled cartridge or carpule can be supplied with an easily removed hermetically sealing cap to keep the external surface sterile, in the event that the cartridge is not supplied in a separate sterile package. Preferably. the trailing end of the cap can be biased to assure easy removal before use of the cartridge.

SUMMARY OF THE INVENTION

We describe a connector for eliminating accidental needle sticks in healthcare workers and minimizing the incidence of nosocomial blood stream infections in patients with skin- or glove-borne microorganisms during the injection of sterile liquid medications into the infusion ports of intravenous access assemblies. Fundamentally, the connector consists of a tubular injector containing a recessed hollow needle sharp on each end. The leading end of the injector will snugly hold the trailing end of an inserted standard elastomer capped intravenous access port. The trailing end will snugly hold the leading of a similar elastomer capped infusion port attached to trailing tubing or a cartridge like a dental carpule with a penetrable diaphragm, a bore containing a specified volume of sterile liquid medication, a cartridge piston and a separate dose-measuring plunger. When assembled such that the trailing cap on the primary infusion port is penetrated by the leading end of the recessed needle and the trailing end of the needle penetrates the leading cap on a second infusion port or the penetrable diaphragm on the cartridge, specified volumes of sterile fluid may be injected into the intravenous access system. By eliminating exposed needles, blunt cannulae, standard syringes, multiple dose vials and ports modified to accept blunt cannulae or syringe nozzles, the connector offers the following advantages for patients: (a) sterile fluid medications the can delivered into the blood stream with minimal chances for contamination with skin-borne microorganisms; (b) low cost for intravenous injection of soluble medications, especially those needing preservation in glass, instead of plastic containers. For healthcare workers the advantages are: (a) convenience; (b) no chances for accidental needlesticks from the recessed needles; and (c) time-cost efficiency. For manufacturers advantages are: (a) opportunities to serve patients and healthcare workers better without changing basic components of standard intravenous infusion systems; (b) opportunities to conveniently provide a variety of IV medications needing preservation in glass containers or dispensation in plastic bags in standard doses measured in terms of mL.

DESCRIPTION OF PREFERRED EMBODIMENTS

Figure 1:
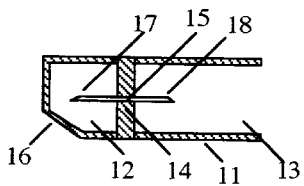
FIG. 1 is mid-axial section of the tubular injector.

FIG. 1 shows a connector 11 comprising a tubular member divided into a leading chamber 12 and a trailing chamber 13 divided by a septum 14 stable-holding a hollow bore steel needle 15 sharp on each end. The leading end of the leading chamber 12 is cut off on a partial bias 16 with respect to the long axis of the tubular member 11. The sharp leading end 17 and sharp trailing end 18 of the needle 15 are recessed in the tubular member such that neither sharp end of the hollow bore needle can be touched by a finger.

Figure 2:
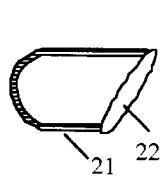
FIG. 2 is a mid-axial section of a cap for the cartridge.

FIG. 2 shows a cap 21 for protecting and hermetically sealing the leading end of a cartridge 31, if the cartridge is not dispensed individually in a sterile package. The trailing end of the cap 21 is cut on a bias 22 to facilitate removal from the leading end of the cartridge 31 just before use.

Figure 3:
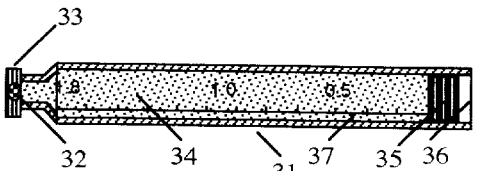
FIG. 3 is a mid-axial section of the cartridge.

FIG. 3 shows a standard dental carpule 31 with a leading penetrable diaphragm 32 held in place by a circumferential metal cap 33; a cavity filled with 1.8 mL. of sterile liquid medication 34; an elastomeric piston 35; and a trailing open end 36. Although not conventional for standard dental carpules, graduated volume markers 0.5 to 1.8 are indicated at 37. The outside diameter of the barrel in standard dental carpules 31 is uniformly 8.5 mm. The outside diameter of the circumferential metal cap 33 is uniformly 8.3 mm. The outside diameter of leading penetrable diaphragm 32 externally exposed for access under the circumferential cap 33 is 3.0 mm. This leaves a circumferential recess for potential bacterial contamination between the penetrable diaphragme and the metal cap all the way around and approximately 7 square mm. of the external surface of the carpule diaphragm exposed to finger or air-borne contamination. Hence, the necessity of supplying the entire carpule sterile on the outside, as well as on the inside; or supplying a removable sealing cap for the 8.5 mm. outside diameter of leading end of the cartridge 31. A sterile package for each cartridge is a convenient and, possibly, preferable alternative to the biased sealing cap 21.

Figures 4, 5:
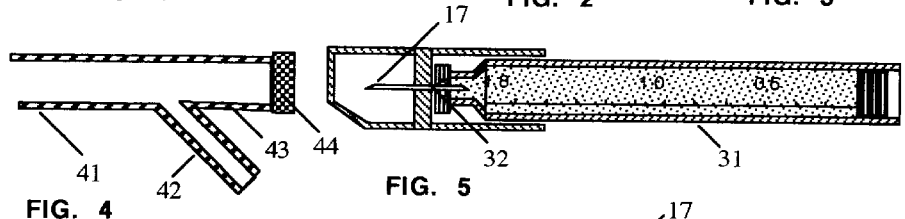
FIG. 4 is a mid-axial section of the Y-infusion port on a traditional IV infusion assembly.
FIG. 5 shows the leading end of the cartridge inserted into the trailing end of the injector.

FIG. 4 shows a traditional Y-infusion port in an intravenous infusion assembly. The Y-port 41 comprises hollow rigid plastic tubing in the form "Y" with one limb 42 conducting main stream infusion fluid from a large volume source, such as sterile 1 L. bag or bottle. The other limb, comprising the port 43 for addition of lesser volumes of liquid medications, is capped by an elastomeric diaphragm 44 through which a sharp hollow bore steel needle is inserted to convey fluid from a syringe or a "piggyback" assembly. Customarily, the elastomeric diaphragm forms a cap which is permanently inserted to plug the trailing end of the infusion port 41 and overlap the outside diameter of the port, such that the external diameter of the port cap is ±8.5 mm. This varies slightly in models fabricated by differing manufacturers, partly owing to the thickness of a plastic sustainer used to compress and hold the cap overlap stable, and partly owing to the thickness of rigid plastic material used to fabricate the port. Such details are not shown here because they are not relevant. That which is important to note is that the outside diameter of the elastomeric diaphragm 44 which caps the infusion port 43 is compressible and usually very close to the outside diameter of a standard carpule 31, i.e. 8.5 mm or slightly larger. Therefore, if the inside diameter of the leading recess 12 in the tubular injector 11 is made 8.6 mm., a snug fit will result. Moreover, if the trailing recess 13 in the tubular injector is made 8.6 mm. a snug fit for the leading end of the cartridge will result, such that injector 11 will securely hold the trailing end of the infusion port 43 and the leading end of the cartridge 31 simultaneously, when assembled.

It should be added here that, but not shown, that the penetrable diaphragms on infusion ports unusually embody a central recess of ±3 mm. diameter and variable length on the main stream side of the infusion assembly to shorten the amount of distance a sharp needle needs to pass through compressed elastomer to gain access to the main stream. Such dimensions are important, because they necessitate proper axial alignment and stabilization of the needle, especially when needles sharp on each end are used for diaphragm penetration.

FIG. 5 shows the leading end of the cartridge 31 advanced into the trailing chamber 13 of the tubular injector 11, such that the leading diaphragm 32 is penetrated by the trailing sharp end of the needle 18 in proper axial alignment guided by a snug fit between the inside diameter of the trailing recess 13 in the injector and outside diameter of the cartridge barrel 31.

Figure 6:
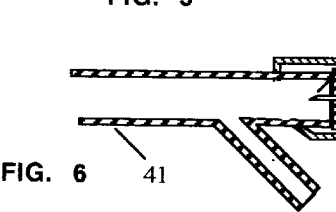
FIG. 6 shows the leading end of the tubular injector inserted over the pentrable port cap.

FIG. 6 shows further advancement of the cartridge 31 and the injector 11 over the penetrable cap 44 and onto the intermittent infusion limb 43 of the Y-port 41, such that the leading sharp end of the needle 17 penetrates the elastomeric cap 44 in proper alignment and the bias 16 on the leading recess 12 of the injector 11 over-rides the other limb 43 of the Y-port 41. The bias, partial as shown here, or all the way across the leading chamber 12 in the tubular injector 11 as shown later, will enhance axial stability by maximizing surface contact between the injector 31 and the Y-port 41.

Figure 7:
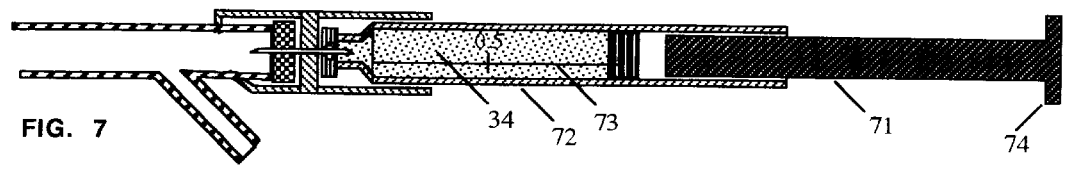
FIG. 7 shows the plunger inserted into the trailing end of a cartridge containing 1.0 mL. of fluid intended for injection into the Y-port.
Figure 15:
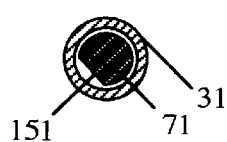
FIG. 15 shows a cartridge plunger suitable for appropriate marking and effective venting.

FIG. 7. shows the cartridge plunger 71 inserted into a cartridge 72 whose liquid contents 34 are limited to 1.0 mL. with corresponding markings 73 on the cartridge 72. This innovation allows adequate space in the open trailing end of the cartridge for stable insertion of a simple plunger 71 whose body length is adjusted to delivery precisely 1.0 mL. before being stopped by a trailing flange 74. The plunger fit to the cartridge bore should be snug, but not snug enough, or should be vented as shown in FIG. 15 to allow the free passage of air between the piston 75 and the trailing end of the cartridge plunger 74.

It should be added here that a 1.0 mL. dose of sterile liquid medication is standard in medical practice. Most doses of chosen medications are calculated on full doses, fractions or multiples thereof. Therefore, this partial filling of the cartridge accomplishes two useful purposes. If a 2.0 mL dose is required, a second cartridge could be used; or, alternatively, the length of the cartridge and the plunger can be adjusted appropriately to inject a larger specified volume without changing the critical diameters of component elements. Another alternative (shown in FIG. 19) is to adjust the inside diameter of the trailing chamber larger to accommodate a cartridge of larger bore and external diameter.

Figure 8:
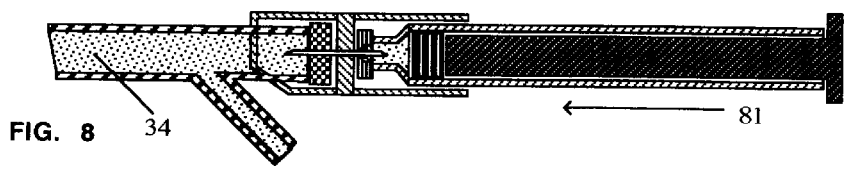
FIG. 8 shows the fluid contents of the cartridge injected into a Y-infusion port.

FIG. 8 shows the injection of 1.0 mL liquid medication 34 into the intravenous infusion assembly activated by manual pressure on the trailing end of the plunger 74 in the direction of the arrow 81 whereby the piston 35 is advanced through the cartridge (carpule) 31 until the piston is stopped from further advancement by a shoulder 38 on the carpule, disposed a stop distance D from the leading penetrable diaphragm 32. It should be emphasized here that no means for attachment of the cartridge plunger to the piston is shown, because attachment would allow the cartridge to aspirate fluid from, as well as inject fluid into the main stream in an intravenous access assembly. Thus, accurate dosimetry might be enhanced, because the dose in the cartridge will not be diluted by fluid emanating from the main stream. It is doubtful that the Venturi phenomenon would be a factor, because main stream coming from the other port 42, usually of smaller diameter, would have sufficient jet effect to displace the cartridge piston.

Figure 9:
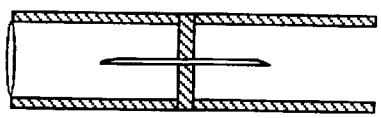
FIG. 9 shows a tubular injector without a bias on the leading end.

FIG. 9 shows a tubular injector 91 without a bias on the leading end of the leading chamber 12. Such a model might be suitable for other kinds of infusion ports lacking second limbs located close to the infusion limb with a penetrable elastomeric cap.

Figure 10:
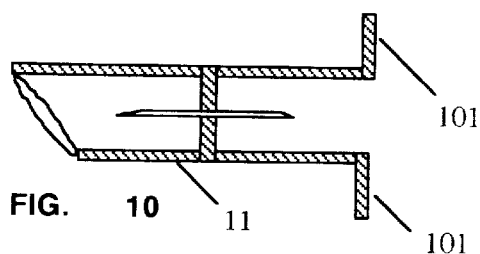
FIG. 10 shows a tubular injector with a bias on the leading end and trailing flanges for finger grasping.

FIG. 10 shows a tubular injector with a leading bias and trailing flanges 101 for finger grasping. Some users might consider this modification more convenient for injecting from a cartridge with one hand; while the other hand stabilizes intervening elements.

Figure 11:
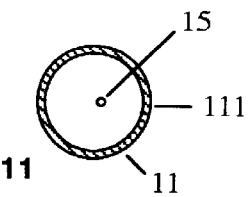
FIG. 11 shows a tubular injector containing an eccentric needle in cross section.

FIG. 11 is a cross section of the tubularinjector 11, showing the needle 15 in an eccentric, instead of concentric position. The injector should be marked externally 111 to indicate the eccentric location of the needle 15. This modification allows the user to change the pathway of needle thrust through the elastomeric cap of the Y-port by axially rotating the connector's position with respect to the port and, thereby, avoid intravenous injection of bacteria which have colonized needle tracts previously used, as well reduce the chances for embolization of elastomer caused by fraying with repeated concentric injections.

Figure 12:
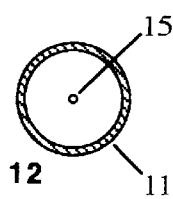
FIG. 12 shows a tubular injector containing a concentric needle in cross section

FIG. 12 shows a concentric needle 15 in the tubular injector 11 for comparison.

Figure 13:
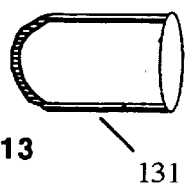
FIG. 13 shows an unbiased cap for the leading end of the cartridge.

FIG. 13 shows a cartridge cap 131 whose trailing end is unbiased, for comparison with the biased counterpart 22 shown in FIG. 1. The latter is simply easier to take off.

Figure 14:
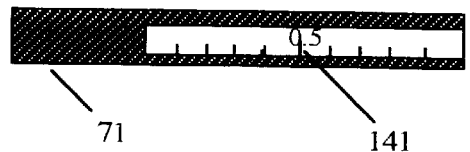
FIG. 14 shows graduated markings on the body of a plunger intended to deliver 1.0 mL. of fluid medication into the infusion port when fully inserted into the cartridge.

FIG. 14 shows graduated markings 141 for injection of 1.0 mL. on the body of the cartridge plunger 71. Such markings facilitate accurate dosimetry, because markings on a clear glass cartridge may be difficult to see with bad light or contained colored solutions.

FIG. 15 shows a plunger 151 flat on one side for marking and for solving problems associated with inadequate venting.

Figure 16:
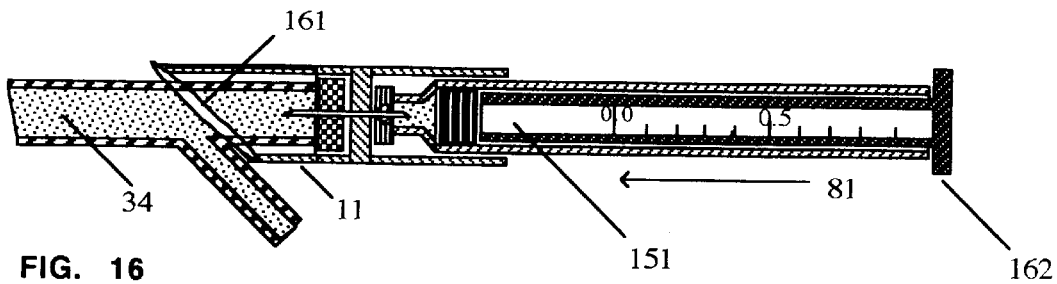
FIG. 16 shows a preferred embodiment of the connector assembled with a cartridge.

FIG. 16 shows a preferred embodiment of the assembled system after use for giving the measured injection 34 into the Y-port on an intravenous access assembly. The biased opening 161 all the way across the leading end of the tubular injector 11 allows firm stabilization of the injector over the Y-port. It will be found in use that the bias allows up to 45° axial rotation of the injector such that the eccentric needle described with FIG. 11 can be rotated through this arc to avoid passage of needle through the same track in penetrable cap of the infusion port. Thus, with appropriate markings on the connector indicating the eccentric location of the needle with respect to the bias 161, the user can plan for variation in the pathway of the needle thrust through the cap. The flat surface of the cartridge plunger shown at 151 extends to the leading end to provide for adequate venting. The markings 0.0 to 0.5 on this surface clearly indicate dosage injected. A trailing flat ring 162 for finger placement on the trailing end of the cartridge plunger is optional. If this flat ring is omitted, as shown in FIG. 14, the trailing end of the cartridge plunger will become flush with the trailing end of the cartridge when a full 1.0 mL. dose of liquid medication is injected from a cartridge having the same dimensions as a standard dental carpule. As noted with FIG. 7, the dimensions of the cartridge and the trailing recess in the tubular injector can be altered to accommodate larger volume doses. However, dental carpules are standard and inexpensive, depending of the cost of the liquid medications contained. Therefore, the dental carpule, partially filled, is used here as a convenient example for construction of the injection system In use of this tubular injector for the sterile liquid contents of a cartridge, the first and most critical step for protection of the patient from intravenous injection of skin- or air-borne microbes is to properly sterilize the exposed surface of the elastomer capping a selected infusion port; and to wait long enough for the chosen antiseptic to exert maximal antimicrobial effect. After this the user:

1. Uncaps the cartridge without touching the leading diaphragm, or removes an uncapped cartridge sterile-packaged separately, or along with the separate cartridge plunger.
2. After removing the injector from the same sterile or a second sterile package, the user inserts the leading end of the cartridge into the trailing recess of the injector until advancement is stopped by the rigid septum in the injector, and the trailing sharp end of the needle has penetrated the sterile diaphragm on the leading end of the cartridge.
3. The user then inserts the elastomer capping the infusion port into the leading chamber of the connector and pushes the infusion port into the injector-cartridge assembly until the leading end of the sharp needle penetrates the infusion port diaphragm and advancement of the injector-cartridge assembly is stopped by the septum in the connector with stabilization of the biased leading end of the connector over the other limb of a standard Y-port.
5. Then, the user inserts the body of the cartridge plunger (which need not be sterile or sterile-packaged with the cartridge) into the open trailing bore of the cartridge, and advances the plunger until its leading end touches the cartridge piston.
6. Then, the user activates the piston by advancing the plunger until the prescribed dose of liquid medication has been discharged into the IV access assembly.
7. Last, the tubular injector-cartridge-plunger assembly, detached from the infusion port by retraction, can be safely disposed conveniently as a unit into an appropriate container. It is optional to remove and reuse the cartridge plunger, but probably preferable to supply a new plunger with each sterile-capped cartridge.

Use of this injector and inserted cartridge into an infusion port lacking a nearby Y-limb or having a T-limb, as in some heparin locks, is similar except a bias on the leading end of the injector would seem to fulfill no useful purpose. Thus, the leading end might be unbiased, as shown in FIG. 9. However, in use, the bias makes it easier to insert the injector over the port, because the leading end of the bias helps to guide the insertion of tube of large size over a tube of smaller size, or a tube of smaller size into one of greater size. With special reference to heparin locks, it should be added that these are usually located very close to veins accessed by a leading needle or a needle-introduced catheter on the intravenous access assembly. Being used intermittently apart from a nearby main infusion stream, they are likely to contain reflux venous blood and, thus, are especially hazardous for health care workers with respect to accidental needlesticks transmitting blood-borne pathogens. At the same time, the heparin locks are especially hazardous for patients, owing to contamination of multiple-dose heparin vials with blood-borne, as well-as skin born pathogens. Thus, this tubular injector and cartridge system might prove especially useful for intermittent intravenous injection of heparin, as well as other soluble medications needing preservation inside glass.

Figure 17:
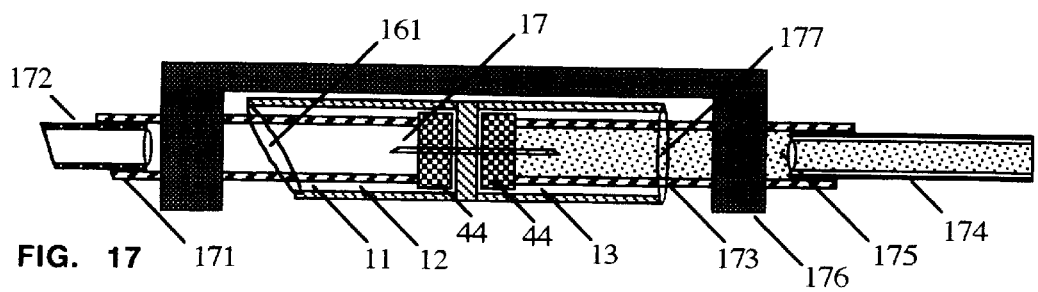
FIG. 17 shows an embodiment of the connector assembled with two similar infusion ports.

An alternative use of the tubular injector without the cartridge is shown in FIG. 17. The tubular injector 11 snugly houses the trailing end of a first inserted infusion port 171 without a Y-limb into the leading recess 12. The leading end of the port 171 is connected to leading tubing 172 coursing toward the actual site of venous access. Instead of a cartridge, in the trailing recess 13, the injector 11 snugly houses a similar penetrable-elastomer capped 44 second infusion port 173 connected to trailing tubing 174. The trailing tubing 174 is terminally attached to a plastic bag or a vented medication bottle (not shown) from whence relatively large measured volumes of sterile fluid medication 175 may flow through the hollow needle sharp on each end 17 under the force of gravity with regulation by an intervening clamp (not shown). Although the system will be found very stable after the elastomeric caps 44 on the first 171 and second 173 infusion ports are penetrated by the needle sharp on each end 17, a separate reusable clamp 176 grasping the exposed ends of each infusion port after connection over the needle is a useful addition for enhancement of stability, especially during occasions when the system is used for extended periods of time. For enhancement of sterility, an easily removed sterile cap (not shown) should be supplied over the elastomeric cap 44 of the second infusion port 173.

Use of this alternative tubular injector should be similar to that previously described, except the user will insert the leading of the second infusion port 173, instead of a cartridge into the trailing recess 13 of the injector 41, and do so before re inserting the trailing end of the first infusion port 171 into the leading chamber 12 of the injector 11. After use, the user will dissemble the system in reverse by disconnecting the first infusion port 171 and, then, the second 173 such that minimal leakage ensues from the hollow needle sharp on each end 17. As combined results, only the injector 11 with a safely recessed needle sharp on each end 17 held in the tubular injector 11 remains to be safely disposed when convenient into a sharps container; while the remaining paraphernalia becomes harmless to the user, as well as the patient.

It should be noted in FIGS. 16 and 17 that the connector 11 is illustrated with a bias 161 entirely across the leading end of the leading chamber 12 of the tubular injector 11; whereas in FIG. 17 the trailing end of trailing chamber 13 of the tubular injector 11 is shown unbiased 177. For user convenience during insertion of the leading first infusion port 171 and the trailing second infusion port 173 in intravenous access systems lacking Y-ports close to the critical infusion sites, it would be preferable to make the leading and trailing ends of the tubular injector 11 biased.

Figure 18:
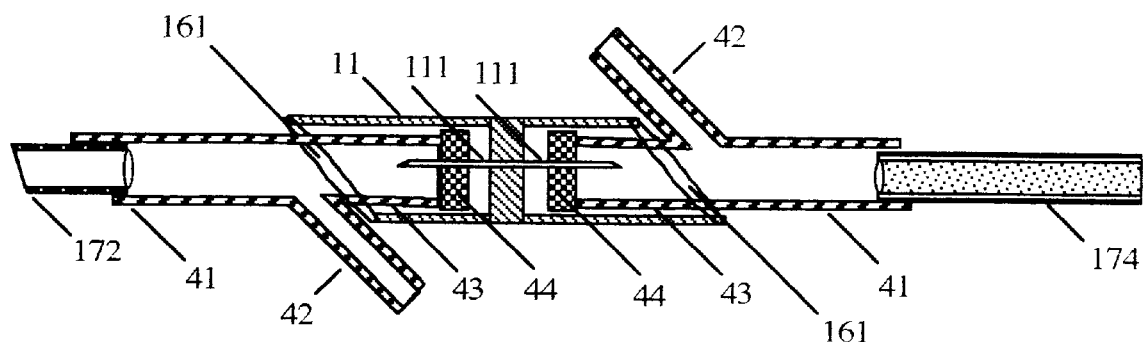
FIG. 18 shows an embodiment connecting two similar Y-infusion ports.

Finally, as shown in FIG. 18, two similar Y-ports 41, one attached to leading tubing 172 and the other attached to trailing tubing 174, can be connected via the tubular injector 11 shown here with an eccentric 111 instead of concentric needle which penetrates both elastomeric caps 44 after axial assembly. In this case, the customary main stream limbs of the Y-ports 42 will become auxiliary ports through which flow can be controlled by appropriate clamping.

Figure 19:
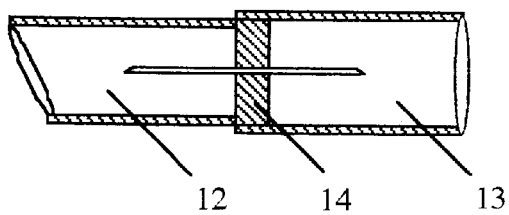
FIG. 19 shows an embodiment where the leading and trailing chambers differ in diameter.

The foregoing specifications are exemplary. Potential variations by experts in the field are many without departing from the spirit of the invention. For instances:

As shown in FIG. 19, the trailing chamber 13 in the connector may be made with an internal diameter larger than that of the leading chamber 12, so as to accommodate insertion of the penetrable cap of a sterile fluid source in the form of a cartridge or the leading end of a large volume source having a relatively large external diameter, for example a medicinal cartridge with a volume capacity greater than that of a standard dental carpule.

Figure 20:
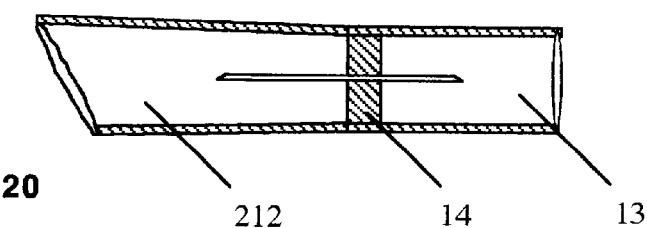
FIG. 20 shows an embodiment wherein the leading chamber is cone-shaped.

As shown in FIG. 20, the leading chamber 212 of the connector may be made in the form of an open-ended hollow cone whose internal diameter decreases in a trailing direction, so as to accommodate insertion of penetrable caps of IV infusion ports made by differing manufacturers with slightly smaller or larger external diameters. An additional desirable feature here is that this coning of the leading chamber will cause the elastomeric caps, irrespective of external diameter within certain limits, to become wedge impacted in the leading chamber 212 and, thus, become held more stable after axial insertion. Because most standard infusion port caps are made of penetrable latex elastomers, compression of the elastomer, itself, against the inside of the relatively rigid connector. It should be added, but not shown here, that the trailing chamber 13 in the connector can be coned similarly, or coned and biased similarly, to accept stable axial insertion of penetrable caps on the leading ends of tubing fed by large volume sterile fluid sources, as described with FIGS. 17–18.

Figure 21:
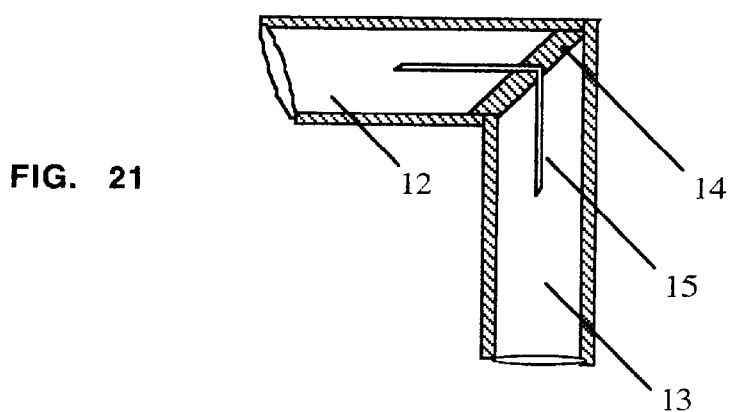
FIG. 21 shows an embodiment wherein the leading and trailing chambers are angulated with respect to one another.

As shown in FIG. 21, the connector might be shaped in the form of an L wherein the leading 12 and trailing chambers 14 are at angles to one another. Here a 90° L is shown with the rigid septum holding the needle sharp on each end 15 contained in a 45° angle with respect to the long axis of each limb.

Finally, from a functional point of view, it should be re-emphasized that the prime object of this invention is sterility of infusions given to patients. Convenience for healthcare workers giving the infusions is secondary. Prevention of accidental needlesticks is tertiary.

Therefore, we claim:

1. A connector for the conveyance of a fluid medication from a cylindrical cartridge to an infusion limb having a penetrable cap disposed on an intravenous access assembly, the cylindrical cartridge being a tube with a central bore having an open trailing end, a leading end sealed by a puncturable septum and a piston slidably disposed within the central bore between the leading end and the open trailing end, and a fluid medication contained in the central bore between the piston and the puncturable septum, wherein when the puncturable septum is punctured by a hollow bore needle and the piston is advanced through the central bore to a stop distance from the leading end of the cylindrical cartridge beyond which stop distance the piston cannot be further advanced, the fluid medication is substantially entirely ejected from the cartridge, said connector comprising:

(a) a tubular injector having a central bore and two open ends, said central bore being subdivided into a leading chamber and a trailing chamber by a rigid septum: and (b) a double-ended hollow bore needle supported by and extending through said septum, said hollow bore needle providing fluid communication between said leading and trailing chambers, said double-ended hollow bore needle having a trailing end with a sharp tip recessed within said trailing chamber and projecting into the trailing chamber from said rigid septum a distance less than or equal to said stop distance, and an opposing end with a sharp tip extending into and enclosed by said leading chamber such that neither end of said double-ended hollow bore needle projects beyond the open ends of said tubular injector, said open ended leading chamber dimensioned to receive said infusion limb therewithin, thereby enabling said opposing end of said hollow bore needle to puncture said penetrable cap on said infusion limb, and wherein at least one of said open ends of said tubular injector is cut on a bias.

* * * * *